United States Patent [19]
Tihon

[11] Patent Number: 5,865,815
[45] Date of Patent: Feb. 2, 1999

[54] PROSTATIC OBSTRUCTION RELIEF CATHETER

[75] Inventor: Claude Tihon, Eden Prairie, Minn.

[73] Assignee: ContiMed, Inc., Eden Prairie, Minn.

[21] Appl. No.: 840,927

[22] Filed: Apr. 25, 1997

[51] Int. Cl.$^6$ .................................................. A61M 25/00
[52] U.S. Cl. ........................... 604/280; 604/265; 604/281
[58] Field of Search .................. 604/8, 264, 280, 604/265, 281, 282, 350, 268, 275, 276

[56] References Cited

U.S. PATENT DOCUMENTS

| 4,307,723 | 12/1981 | Finney .................................... 604/8 |
| 4,479,795 | 10/1984 | Mustacich et al. ....................... 604/53 |
| 4,531,933 | 7/1985 | Norton et al. ............................. 604/8 |
| 4,610,657 | 9/1986 | Densow .................................... 604/8 |
| 4,671,795 | 6/1987 | Mulchin .................................. 604/281 |
| 4,799,474 | 1/1989 | Ueda ........................................ 128/4 |
| 5,354,263 | 10/1994 | Coll .......................................... 604/8 |
| 5,591,145 | 1/1997 | Sachse ....................................... 1/1 |
| 5,647,843 | 7/1997 | Mesrobian et al. ...................... 604/8 |
| 5,681,274 | 10/1997 | Perkins et al. ........................... 604/8 |

Primary Examiner—Wynn Wood Coggins
Assistant Examiner—Deborah Blyveis
Attorney, Agent, or Firm—Haugen and Nikolai, P.A.

[57] ABSTRACT

A prostatic obstruction relief catheter for insertion in the urethra of a male patient comprises an elongated, flexible, tubular, plastic catheter body having a generally cylindrical wall where along its length it is partitioned into a bladder retention zone, a prostate gland spanning zone, a zone designed to cooperate with the urinary sphincter and a fourth zone extending at least partially through the pendulous penis. The tubular catheter body has a plurality of radially extending bores through its wall and in fluid communication with a lumen, whereby urine collected in the bladder may readily bypass a patient's enlarged prostate gland while being controlled by his urinary sphincter to thereby maintain continence.

12 Claims, 5 Drawing Sheets

PROSTATIC OBSTRUCTION RELIEF CATHETER

BACKGROUND OF THE INVENTION

I. Field of the Invention

This invention relates generally to a urinary catheter, and more particularly to a urinary catheter for temporary relief of symptoms due to benign prostatic hypertrophy (BPH).

II. Discussion of the Prior Art

Enlargement of the prostatic gland is common among men after 50 years of age. The condition is not malignant nor inflammatory, but may lead to obstruction of the urethra, interfering with the flow of urine. This can increase frequency of urination, the need to urinate during the night, pain and urinary tract infections.

The prostate gland itself is somewhat walnut-shaped and surrounds the urethra just below the neck of the urinary bladder. With BPH, the prostate may significantly narrow the urethra causing the above problems. A procedure called transurethral resection of the prostate is often used to remove some of the tissue comprising the prostate gland to reduce its size and thereby leave the urethra unobstructed. Because of the discomfort associated with this surgery, many males shun it until the process progresses to the point where a drainage catheter, such as the well known Foley catheter, is used to continuously drain the urinary bladder into a urine collection bag. A Foley catheter comprises a double lumen tube adapted to be inserted into the urethra through the meatus thereof and advanced until its distal end resides in the urinary bladder. The first lumen comprises an inflation lumen for causing an expandable balloon on the distal end portion of the catheter to be inflated. The inflated balloon serves to hold the drainage catheter in place. There is an opening at the distal end of the second lumen through which urine can flow through the length of the catheter to the collection bag. With such a catheter installed, the patient has no control over the elimination of urine from the bladder.

The Foley catheter has another drawback. Because urine drips through the lumen of the catheter, the walls of the urethra are not periodically bathed during urination, resulting in an increase in urinary infection. Thus, the catheter must be periodically removed and replaced to avoid the growth of bacteria between the wall of the catheter and the lining of the urethra.

A need therefore exists for draining the bladder without the above-recited difficulties associated with the use of a Foley catheter. The device must maintain the prostatic urethra patent in patients with BPH while still allowing the patient to utilize his urinary sphincter for controlling the elimination of urine from the bladder. The device should also permit it to be disposed in the patient's urethra for extended periods without increasing the likelihood of infection.

SUMMARY OF THE INVENTION

It is accordingly a principal object of the present invention to provide an improved prostatic obstruction relief catheter for patients suffering from BPH which overcomes substantially all of the deficiencies of the Foley catheter.

The prostatic obstruction relief catheter of the present invention comprises an elongated, flexible, tubular, plastic catheter body dimensioned to readily pass up the urethra and having a generally cylindrical wall, a proximal end and a distal end. The catheter body is partitioned into a plurality of zones including a first zone adapted for placement in the patient's urinary bladder which, when unconstrained, assumes a flat spiral shape and functions to retain the catheter in place. Contiguous with the first zone is a second zone adapted to span the patient's prostate gland when the first zone is located in the patient's urinary bladder. Directly contiguous with the second zone is a third zone that is adapted to span the patient's urinary sphincter. The flexible tubular plastic catheter also has a fourth zone contiguous with the third that leads toward the urinary meatus. The tubular body further includes a first, larger lumen in the first, second and fourth zones through which urine may pass. A second, smaller lumen for receiving a stylet therein is also provided and extends through all four zones. Extending through the wall of the tubular catheter body and in fluid communication with the larger lumen are a plurality of apertures located in the first, second and fourth zones allowing outflow and inflow of urine from and to the larger lumen. The third zone that is adapted to cooperate with the urinary sphincter controls the flow of urine from the second zone to the fourth zone.

Because of the above-described configuration, in the fourth zone by the pressure of the urethral wall, urine is directed to flow through the larger lumen of the tubular catheter body. Zone 4 can be reduced in length such that it terminates within the urethra. In this fashion, urine, once it is released from the bladder by relaxing the urinary external sphincter, can effectively cleanse the urethra as the normal physiology and anatomy function. This urine flow tends to wash away bacteria each time the patient releases his urinary sphincter to drain the bladder in a bolus fashion. By impregnating the tubular plastic body of the catheter with a suitable self-eluting drug, infection or other problems of the urinary tract can be treated.

In the case where it is desirable for urine to be continuously drained from the bladder, zone 3 may be eliminated such that zone 2 becomes contiguous to zone 4. It is desirable that, in such a catheter, a collection bag be connected to the portion of the single-lumen tube exiting the meatus.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
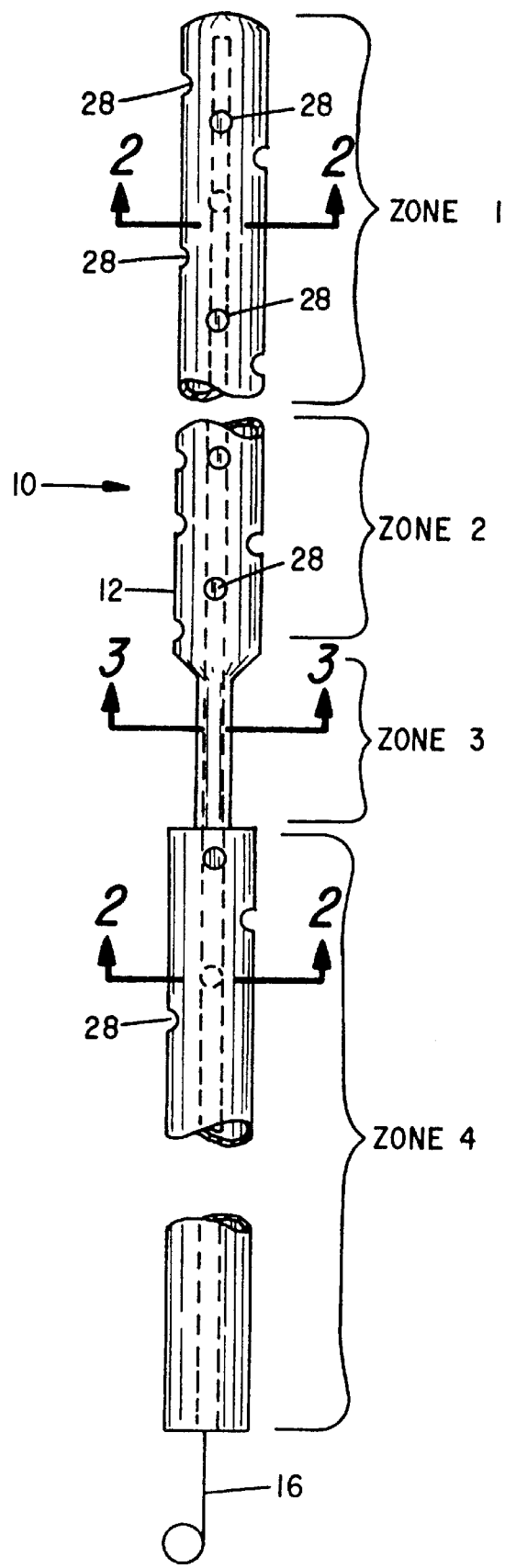
FIG. 1 is a side elevational view of the catheter comprising a preferred embodiment of the present invention when straightened by a stylet for insertion into the patient's urethra.

Referring to FIG. 1, there is indicated generally by numeral 10 a prostatic obstruction relief catheter comprising a preferred embodiment of the present invention. It is seen to comprise an elongated multi-lumen, plastic tubular member 12 whose outside diameter allows it to be inserted through the meatus of the urethra and advanced there along. With no limitation intended, the plastic material comprising the prostatic obstruction relief catheter 10 may be a thermoplastic or silicone or a mixture of thermoplastic, memory alloy and silicone to achieve a desired softness with a durometer of about 60–25 Shore A to permit insertion, removal and prolonged periods of placement within the urethra without causing undue irritation to the endothelial cells of the urethra. The plastic may also be impregnated with a self-eluting drug.

To aid in the insertion of the catheter, it preferably includes a stylet lumen 14 extending the length thereof into which a wire stiffening stylet 16 may be inserted to maintain the catheter rectilinear. Alternatively, the catheter can be maintained rectilinear for insertion by using a tubular stiffening sheath surrounding the catheter and following catheter placement, the stiffening sheath can be removed, allowing the catheter in zone 1 to form into its curl.

Figure 4:
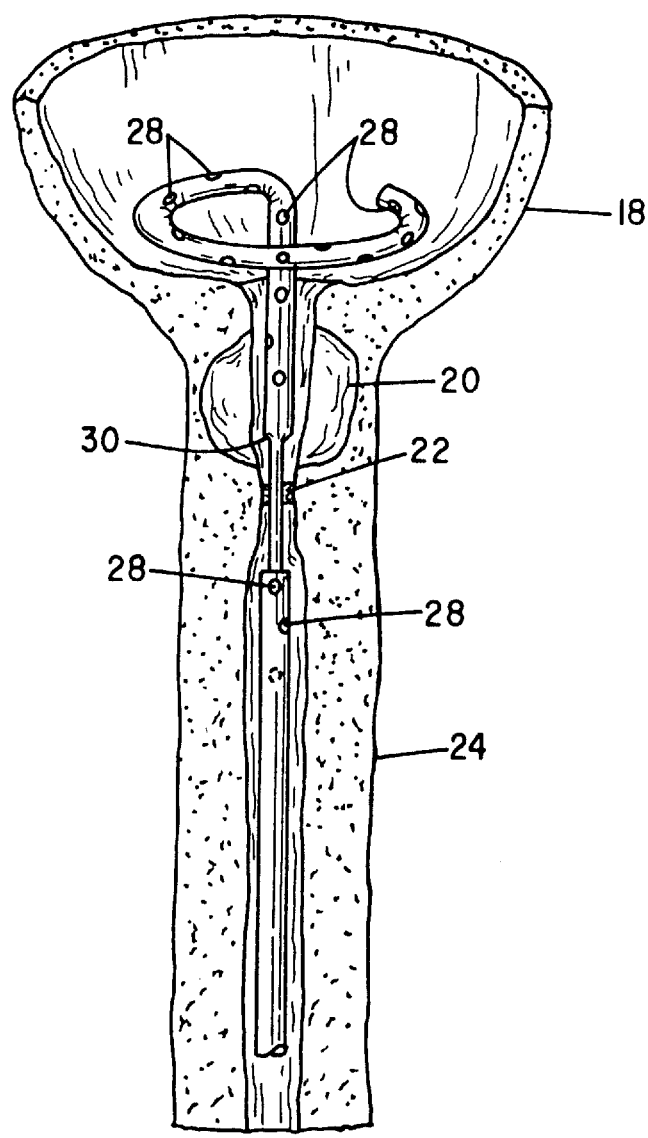
FIG. 4 is an anatomical sketch showing the catheter of the present invention in place in the patient's urinary tract.

As illustrated in FIG. 1, the prostatic obstruction relief catheter 10 may be considered as being divided into four contiguous zones as identified by the brackets labeled "zone 1" through "zone 4", respectively. The portion labeled "zone 1" is adapted to reside in the urinary bladder following the insertion thereof. At least one material comprising the catheter body 12 possesses a memory property, at least in zone 1, such that when the stylet 16 is withdrawn following the insertion of the device, the portion in zone 1 assumes a flat, spiral configuration, the plane of which is generally perpendicular to the longitudinal axis of the remaining portion of the catheter device 10 when unconstrained in the bladder. While temperature annealing of the plastic in zone 1 may be used to induce the desired memory property, a strand 17 (FIG. 2) of shape memory alloy, such as a Nitinol wire, may be embedded in the plastic to cause it to curl into a flat spiral when unconstrained in the bladder. In FIG. 4, a section of the urinary bladder is identified by numeral 18 and the portion of the catheter device comprising zone 1 resides within the urinary bladder as illustrated. With continued reference to FIGS. 1 and 4, contiguous with zone 1 is zone 2 which is dimensioned lengthwise to span the patient's prostate gland 20 when the spiral portion comprising zone 1 is disposed within the urinary bladder 18 as illustrated in FIG. 4.

Contiguous with zone 2 and moving in the proximal direction therefrom is zone 3 which is of different and preferably a reduced cross-section. Zone 3 is dimensioned lengthwise so as to span the patient's urinary sphincter 22 when the portion of zone 2 is bridging the prostate gland. Contiguous with zone 3 is zone 4. It is dimensioned to extend along the urethra through the pendulous portion of the penis 24 for a predetermined distance so as to either exit the meatus of the urethra or to remain totally indwelling.

Figure 2:
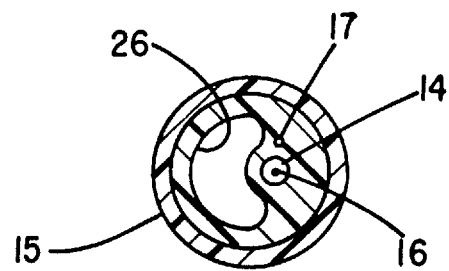
FIG. 2 is a cross-sectional view taken along the line 2—2 in FIG. 1.
Figure 3:
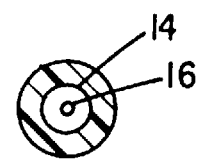
FIG. 3 is a cross-sectional view taken along the line 3—3 in FIG. 1.

As is shown by the cross-sectional views of FIGS. 2 and 3, in zones 1, 2 and 4, the catheter has a larger lumen 26 for accommodating the flow of urine therethrough. The stylet lumen 14 is blocked at its distal end to prevent the stylet 16 from extending out from the distal end of the catheter body 12 where it could otherwise potentially puncture the wall of the bladder. FIG. 2 also illustrates that the catheter body may comprise an inner layer of a more firm material for maintaining the shape of the catheter body and an outer layer 15 of a softer, lower durometer to provide improved patient comfort.

With further reference to FIGS. 1 and 4, it can be seen that in zones 1, 2 and 4, the tubular catheter body 12 has a plurality of longitudinally spaced, radially extending bores, as at 28, that extend through the wall of the catheter so as to be in fluid communication with the lumen 26 thereof. The bores 28 preferably are arranged in a spiral pattern along the length of zones 1, 3 and 4 so as not to unduly weaken the tensile strength of the catheter body 12.

With reference to FIG. 4, urine collected in the bladder 18 may flow through the multiple bores formed in the catheter body in zones 1 and 2 and progress down the lumen 26 to zone 3 where the catheter interfaces with urinary sphincter 22. Here, the catheter is of a lesser diameter and zone 3 is void of the lumen 26. The urinary sphincter functions to compress the walls of the urethra 30 against the O.D. of the catheter in zone 3 to thereby preclude urine flow beyond the sphincter. As in normal urinary function, when the patient having the catheter of the present invention installed relaxes his urinary sphincter, urine from the bladder and in the lumen of the catheter disposed distally of the sphincter is allowed to flow between the necked-down portion of the catheter comprising zone 3 and the urethra to be later at least partially collected through the radial bores 28 in zone 4 so as to flow down through the lumen 26 and along the interface between the O.D. of the catheter and the urethral wall and ultimately out the meatus of the urethra.

Figure 5:
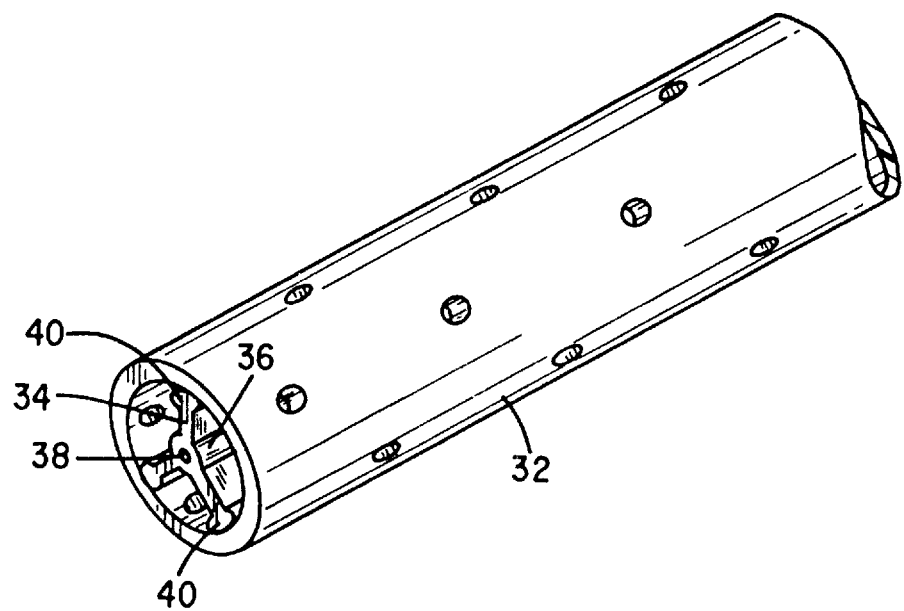
FIG. 5 is a partial perspective view of an alternative construction of a prostatic obstruction relief catheter.
Figure 6:
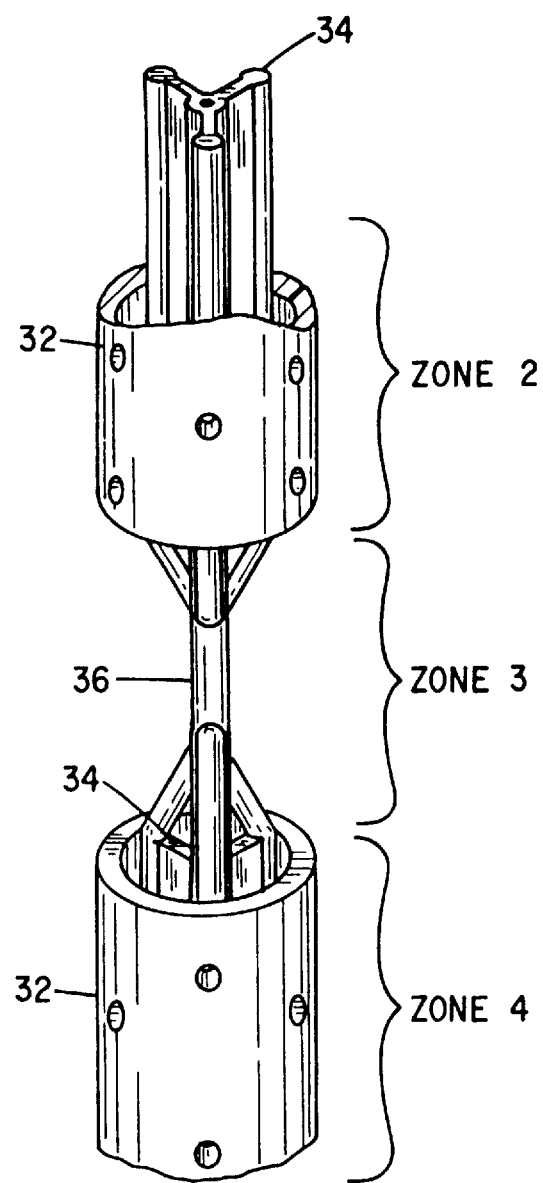
FIG. 6 is a further perspective view of the device of FIG. 5.

An alternative construction of the prostatic obstruction relief catheter is illustrated in FIGS. 5 and 6. FIG. 5 is a partial perspective view of the tubing comprising zones 1, 2 and 4 and is seen to comprise an outer soft, flaccid sheath 32 supported by an internal support member 34. The support member 34 is shown as including a central tubular portion 36 having a lumen 38 extending the length thereof and with three radially extending legs as at 40 at 120° spacing. The support member is preferably formed from a soft plastic such as silicone rubber but which has sufficient rigidity to support the thin-walled sheath 32 so as to define three separate lumens through which urine may flow.

The lumen 38 formed lengthwise through the central tubular portion 36 of the support member 34 is designed to receive a stiffening stylet so that the portion thereof comprising zone 1 can be straightened during insertion of the catheter. As before with the embodiment of FIG. 1, when the stylet is removed from the lumen 38, the portion of the catheter comprising zone 1 may return to a flat spiral configuration for maintaining the catheter in place.

The partial perspective view of FIG. 6 illustrates the way in which zone 3, designed to cooperate with the patient's urinary sphincter, can be implemented. As is apparent in FIG. 6, the legs 40 of the internal support member 34 are tapered down to the outer diameter of the central tubular portion 36 thereof in zone 3.

The operation of the alternative device shown in FIGS. 5 and 6 is substantially the same as when using the embodiment of FIG. 1. Again, urine collected in the bladder will flow through the plurality of apertures formed through the wall of the sheath 32 and will progress down the multiple lumens defined by the plural legs 40 of the inner support member 34 and the sheath 32. Upon reaching zone 3, the legs of the inner support member are tapered to the outer diameter of the central tubular portion 36 thereof and it is that portion that cooperates with the patient's urinary sphincter in controlling urine flow proximal of that location. On relaxing of the urinary sphincter, urine will flow through zone 3 and into the open distal end of the sheath 32 in zone 4 where it is partially collected through the apertures in the sheath so as to flow down through the multiple lumens and along the interface between the O.D. of the catheter and the urethral wall until it flows out from the urethral meatus.

The utilization of two different materials for the construction of the catheter allows the catheter to be very soft on the outside and yet retain its substantive structure for (1) stenting the urethra, especially the prostatic urethra, open for urine drainage, and (2) forming the memory property essential for curl (spiral) to maintain its shape in the bladder. Such a catheter with this basic feature of softness of the surface material, yet with sufficient structural support internally, can be used to stent other body lumens as well.

Those skilled in the art will appreciate that the prostatic obstruction relief catheter of the present invention affords the following advantages over conventional bladder drains such as the well-known Foley catheter:

1. The patient retains control over the release of urine, obviating the need for a collection bag;

2. The retention spiral comprising zone 1 lays relatively flat within the urinary bladder, preventing the type of irritation that results with the Foley catheter when the bladder is in continual contact with the aperture stem that is distal of the balloon anchor on that device;

3. Excretions from the prostate gland as well as urine is able to pass through the catheter;

4. The interior wall of the urethra is exposed to the flow of exiting urine when the patient relaxes his sphincter whereby urine washes the walls of the urethra and, thus, the entry and advance of infection causing bacteria is inhibited.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A prostatic obstruction relief catheter comprising:

(a) an elongated, flexible, tubular, plastic catheter having a generally cylindrical wall and adapted for insertion in the urethra of a male patient, the catheter having a proximal end, a distal end and partitioned into a plurality of zones including a first zone adapted for placement in the patient's urinary bladder, a second zone contiguous with the first zone and adapted to span the patient's prostate gland when the first zone is located in the patient's urinary bladder, a third zone contiguous with the second zone adapted to span the patient's urinary sphincter when the second zone spans the patient's prostate gland and a fourth zone contiguous with the third zone and leading toward the urinary meatus; and (b) the catheter including a first lumen only in the first, second and fourth zones and a plurality of apertures extending through the cylindrical wall and leading to the lumen in the first, second and fourth zones, the first zone of the catheter comprising a bladder retention means; the third zone adapted to cooperate with the urinary sphincter for controlling flow of urine from the second zone to the fourth zone.

2. The prostatic obstruction relief catheter of claim 1 and further including a stylet lumen extending longitudinally through zones 4, 3, 2 and partially into zone 1.

3. The prostatic obstruction relief catheter of claim 2 wherein the catheter is preformed in zone 1 to assume a flat spiral shape when unconstrained.

4. The prostatic obstruction relief catheter of claim 3 and further including a relatively stiff stylet which when fully inserted into the stylet lumen maintains the catheter in zone 1 rectilinear for ease of placement of the catheter in a patient's urinary tract.

5. The prostatic obstruction relief catheter of claim 1 wherein the cylindrical wall of the catheter has a different outside diameter in zone 3 than in zones 1, 2 and 4.

6. The prostatic obstruction relief catheter of claim 5 wherein the outside diameter in zone 3 is less than in zones 1, 2 and 4.

7. The prostatic obstruction relief catheter of claim 1 and further including an outer tubular sheath surrounding the catheter for maintaining the catheter in zone 1 rectilinear for ease of placement in a patient's urinary tract.

8. The prostatic obstruction relief catheter of claim 3 wherein a Nitinol wire is embedded into the plastic catheter in zone 1 thereof.

9. The prostatic obstruction relief catheter of claim 2 in which the plastic catheter comprises a soft, flaccid, tubular sheath and an internal support member disposed within the tubular sheath, the tubular sheath and the support member cooperating to define a plurality of lumens including the first lumen.

10. The prostatic obstruction relief catheter of claim 9 wherein the stylet lumen is formed longitudinally in the support member.

11. The prostatic obstruction relief catheter of claim 9 wherein the tubular sheath is impregnated with a self-eluting drug.

12. The prostatic obstruction relief catheter of claim 1 and further including a collection tube detachable secured to the tubular catheter in the fourth zone.

\* \* \* \* \*